United States Patent [19]

Karakawa

[11] Patent Number: 5,543,115

[45] Date of Patent: Aug. 6, 1996

[54] SPECIMEN HANDLING DEVICE

[75] Inventor: Fuminari Karakawa, Kurume, Japan

[73] Assignee: Mizuho USA, Inc., San Diego, Calif.

[21] Appl. No.: 502,883

[22] Filed: Jul. 17, 1995

[51] Int. Cl.$^6$ ............................ B01L 11/00; G01N 33/72
[52] U.S. Cl. ................... 422/102; 422/56; 422/58; 422/61; 422/101; 436/66; 436/176; 435/269; 435/810; 128/759
[58] Field of Search ................... 422/56, 58, 61, 422/101, 102; 436/66, 176, 177; 435/269, 294, 296, 810; 128/749, 757, 759

[56] References Cited

U.S. PATENT DOCUMENTS

| | | | |
|---|---|---|---|
| 3,651,926 | 3/1972 | Elfast | 206/456 |
| 4,562,043 | 12/1985 | Mennen et al. | 422/56 |
| 4,849,173 | 7/1989 | Chang | 422/56 |
| 4,859,610 | 8/1989 | Maggio | 422/102 |
| 4,978,504 | 12/1990 | Nason | 422/61 |
| 5,066,463 | 11/1991 | Chang | 422/56 |
| 5,149,506 | 9/1992 | Skiba et al. | 422/102 |
| 5,242,660 | 9/1993 | Hsei | 422/102 |
| 5,334,348 | 8/1994 | Saito et al. | 422/61 |
| 5,431,884 | 7/1995 | McDonough et al. | 422/101 |

*Primary Examiner*—Jill Warden
*Assistant Examiner*—Harold Y. Pyon
*Attorney, Agent, or Firm*—Campbell & Flores, LLP

[57] ABSTRACT

This invention relates to a specimen handling device for collecting, storing, processing and dispensing of samples. The invention provides for the collection of specimens from any solid or semi-solid material, including biological samples, food samples, waste samples or soil samples.

11 Claims, 2 Drawing Sheets

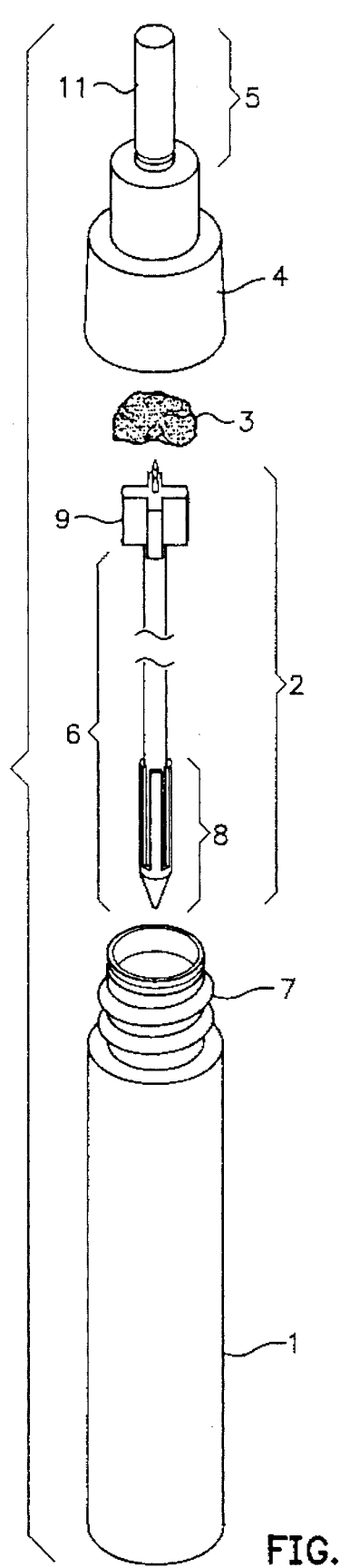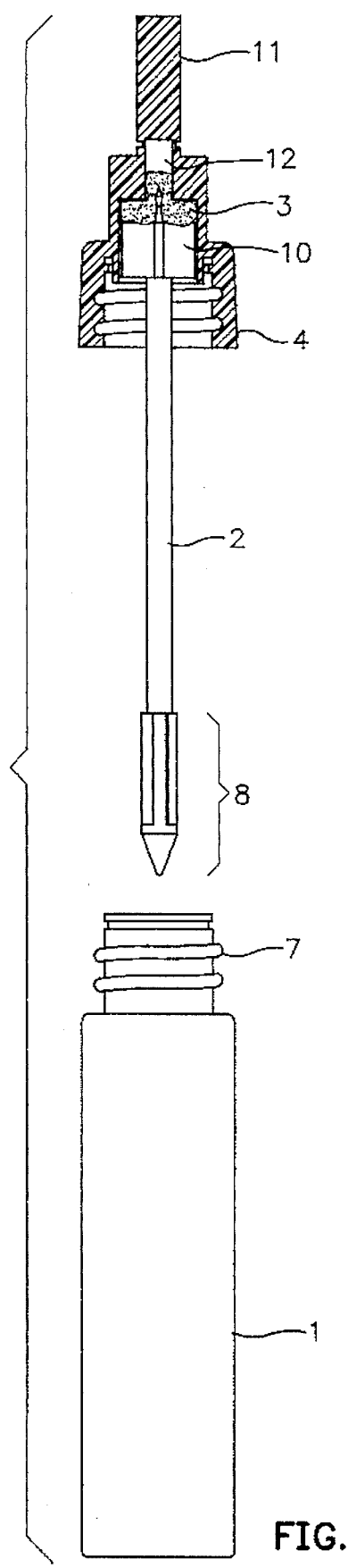
FIG. 1
FIG. 2

SPECIMEN HANDLING DEVICE

BACKGROUND OF THE INVENTION

1. Field of the Invention

This invention relates to a specimen handling device for collecting, storing, processing and dispensing of samples, and, more specifically, to a device used in the analysis of fecal samples.

2. Background Information

The sampling and testing of fecal specimens for the presence of blood elements, such as hemoglobin or transferrin, provides important information for the early detection and diagnosis of diseases, especially conditions associated with gastrointestinal (GI) bleeding. Such testing detects bleeding that originates anywhere from the mouth to the anus. GI bleeding can be caused by a variety of conditions including infections, duodenal ulcers, carcinomas, polyps, colitis, hemorrhoids and angiomas.

Several methods, including conventional chemical tests and more recent immunoassay tests, have been used to detect occult blood in feces. Tests based on chemical reactions with components of the human occult blood analyte, such as guaiac test and the o-toluidine test, have the inherent problems of false negatives and positives. Such incorrect results arise from cross-reaction of the assay's reagents with degradation products similar to the analytes to be assayed as well as with non-human components that are present due to dietary intake by the patient. For example, the hemoglobin from beef and pork ingested by the patient will also cause a chemical assay to register a (false) positive result. The necessary dietary restrictions imposed on patients to eliminate dietary interference make them inconvenient to use.

By comparison, more recent immunoassays have claimed to solve such diet-based cross-reactivity problems, but many of these tests present a different set of problems. In particular, it has been found that hemoglobin in fecal samples is degraded by the intestinal flora also present in the sample. Sufficient time often lapses between the point that the fecal sample is obtained and the point that the hemoglobin is performed on the sample for the hemoglobin analyte to be degraded by the intestinal flora. For example, Enterobactericae or proteases in a fecal sample will convert hemoglobin to globulin, and the globulin will be undetected by the anti-hemoglobin antibodies in the assay. The degradation causes the assay to render a false negative result.

S. Okuda et al., in U.S. Pat. No. 4,920,045, issued Apr. 24, 1990, herein incorporated by reference, described a two-step approach to solve the problems of hemoglobin-based immunoassays: 1) store the fecal sample in a solution of a glycosidase-type bacteriolytic enzyme until the assay is performed, and 2) also simultaneously detect the human transferrin present in the sample with anti-transferrin antibodies. The glycosidase-type enzyme inhibits the activity of hemoglobin-degrading enzymes in the sample. The transferrin analyte is essentially resistant to such enzymatic degradation.

Thus, for the improved assay such as those of Okuda et al. to work, a sampling device is needed that would immediately bring the fecal sample into contact with a stabilizing solution, and maintaining that contact until the immunoassay is performed. Furthermore, the device should conveniently provide a fixed volume of sample, in order to insure the accuracy of a quantitative or semi-quantitative assay, for example, an immunoassay. As human and veterinary samples often contain infectious biological agents, the device should be designed to prevent human contact with the collected sample during the storage and transportation of the sample, as well as during any further processing of the sample in conjunction with the assay. As a corollary, the device should be economical so as to be disposable, eliminating the need for cleaning and sterilization, and also so as to add a minimum to the total cost of performing the assay. Finally, the device should be simple enough to used by the lay individual in the home, the field, or the like, as trained individuals are usually not the ones who would be using the device. For instance, fecal samples are often collected by the patient in his or her own home. The present invention satisfies these needs and provides related advantages as well.

SUMMARY OF THE INVENTION

This invention provides a sample handling device for the collection, storage, processing and dispensing of samples which comprises a sample storage means, a sample collection means, a filter means, a sealable cap and an applicator means. The sample storage means is of a length longer than the sample collection means and has one opening containing a sealing means upon which attaches the above-mentioned sealable cap. As to the sample collection means, it comprises an elongated shaft with a grooved sample collection means at one end and a cap end attached to said sealable cap, wherein the grooved sample collection means contains a plurality of grooves extending parallel to and along the length of the elongated shaft. The fore-mentioned sealable cap has a hollow interior through which sample flows from the sample storage means to the applicator means. Within the sealable cap is the filter means contained through which liquid passes to flow from said sample storage means to the applicator means. The applicator means has a removable applicator tip with a hollow core where displacement of said applicator tip creates an opening on the top of said sealable cap.

BRIEF DESCRIPTION OF THE DRAWINGS

FIG. 1 is a perspective view of the individual components of the specimen handling device.

FIG. 2 is a sectional view of the specimen handling device.

DETAILED DESCRIPTION OF THE INVENTION

Figure 3:
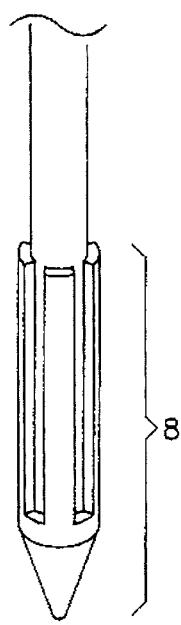
FIG. 3 is a perspective view of the grooved sample collection means end of the elongated shaft illustrating a plurality of grooves formed by projections or indentations. These grooves run along the length of, parallel to, the elongated shaft.
Figure 4:
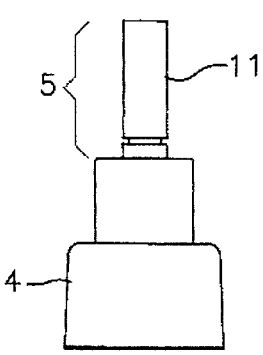
FIG. 4 is a perspective view of the applicator with the removable applicator tip attached.

This invention is directed to the sample handling device set forth above in the Summary.

The components of the specimen handling device of this invention are illustrated in FIGS. 1 and 2. FIG. 1 illustrates the separate components of the device, which includes a sample storage means 1, a grooved sample collection means 2, a filter means 3, a sealable cap 4 and an applicator means 5.

Figure 7:
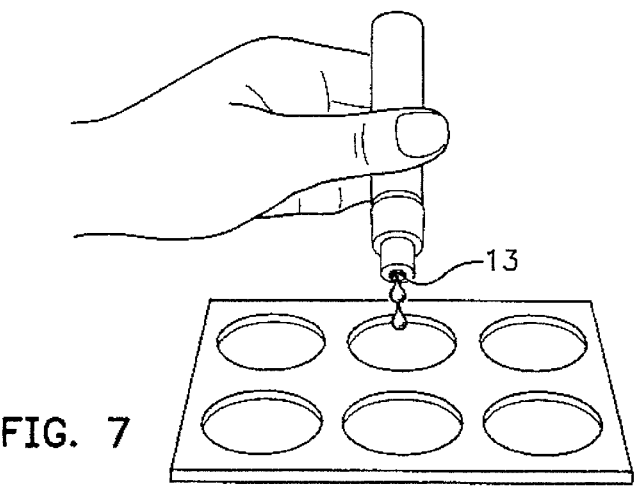
FIG. 7 is a view of the specimen handling device, with applicator tip removed, dispensing sample, in a dropwise fashion, through the applicator tip opening into a testing plate well.

The sample storage means 1, as illustrated in FIGS. 1 and 2, is substantially in the form of a vial, hereinafter referred to as vial 1. The vial 1 is manufactured from any flexible inert material, including polyethylene. The material is flexible to prevent breakage and to allow positive pressure to be applied for the dispensing of liquid sample, as illustrated in FIG. 7.

The grooved sample collection means 2, hereinafter referred to as a sampling stick 2, comprises an elongated shaft 6 which fits within the vial 1, as seen in FIGS. 1 and 2. The vial 1 has one opening with a sealing means which attaches to the sealable cap 4, as illustrated in FIG. 1. This sealing means, or fitting, is leak-proof and can be a screw-on fitting 7, a snap-on fitting, or the like. One end of the elongated shaft 6 has grooves 8. The opposing end is a cap fitting means 9. The grooves 8 comprise a plurality of grooves or indentations running parallel to, along the length of, the elongated shaft 2, as highlighted in FIG. 3. The grooves can be placed along the entire length of the shaft, only near the end of the shaft, or any variation therein.

The sealable cap 4 has a hollow interior, or bore, 10 through which liquid can flow from the vial to an applicator tip 11, as illustrated in FIG. 2. The applicator tip 11 has a hollow bore at its point of attachment to the sealable cap 4. A filter means 3, such as a sponge or a screen, is contained entirely within the sealable cap's interior 10.

The applicator means 5 comprises a removable applicator tip 11 with a hollow core 12 that has a relatively narrow bore, as illustrated in FIGS. 1 and 2. Thus, upon displacement or removal of the applicator tip 11, the hollow core 12 is exposed and an opening 13 is created through which liquid sample can pass in a controlled, dropwise manner, as illustrated in FIGS. 4–7.

Figure 5:
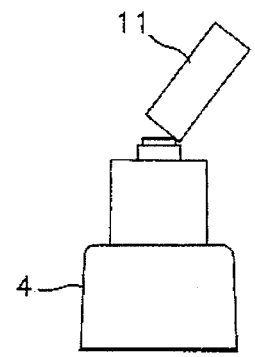
FIG. 5 is a view of the applicator with the removable applicator tip partially broken off.
Figure 6:
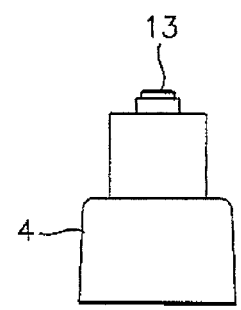
FIG. 6 is a view of the applicator tip with the removable applicator tip completely removed, exposing the hollow core as an opening.

The sample is collected in the channels between the grooves 8 at the end of the sampling stick 2, as highlighted in FIG. 3. Upon insertion into the vial 1, the grooves 8 are immersed into the optional liquid sample-stabilizing reagent. The grooves 8 provide a convenient method of obtaining a fixed volume of sample, as will be set forth in more detail below. After sealing the cap 4 onto the vial 1, agitation of the specimen handling device dilutes and disperses the sample into the liquid sample-stabilizing reagent. Because the vial is composed of a flexible material, positive pressure can be applied to expel liquid through the filter means 3, the applicator means 5, and out the applicator tip after the tip has been displaced or removed as illustrated in FIGS. 5 and 6. The collected sample is filtered as it passes through the filter means 3, and can be applied directly from the specimen handling device into an assay system without further processing, handling or instrumentation, as illustrated in FIG. 7. Thus, the liquid sample can be dispensed into testing plate wells in a controlled, drop by drop, manner, as illustrated in FIG. 7. The applicator tip 11 can be displaced or broken off with only slight application of shear, or lateral, force. The applicator tip can be only partially displaced, with the degree of partial displacement determining the size of the opening on the top of the sealable cap. Thus, as the size of the opening can be varied, the size of the drops dispensed from the collection device can be correspondingly varied, as illustrated in FIG. 7.

The sample collecting means 2 and the sealable cap 4 may be made from any rigid or semi-rigid material, such as natural or synthetic polymers. All that is required of these materials is that they do not interact with the sample and are able to maintain their shape.

Preferred embodiments of the above specimen handling device include wherein the filter means is selected from the group consisting of a sponge material or a screen material, and especially so when it is a sponge material made of polyurethane.

Further preferred embodiments are when the sample storage means is polyethylene, the sample collection means is polystyrene, and the sealable cap is polypropylene.

Other preferred embodiments include those wherein the sample storage means 1 contains a liquid sample-stabilizing reagent, and more so when such reagent stabilizes hemoglobin. Preferred embodiments for such device where the reagent stabilizes hemoglobin is where the reagent is a glycosidase capable of lysing bacterial cells. It is understood to one skilled in the art that such a glycosidase does not decompose hemoglobin prior to the sample's analysis by an assay. Further preferred embodiments include those where the glycosidase is lysozyme. Yet another preferred embodiment for such device wherein the liquid sample-stabilizing reagent that stabilizes hemoglobin is sodium azide in Tris buffer.

The invention can be used with an assay system for determining the presence or quantity of at least one analyte. The assay system can be in the form of a kit, and can comprise 1 specimen handling device of the invention and an assay system for determination of the presence or quantity of at least one analyte. Such analytes may include any inorganic or organic chemical species, biological molecules such as enzymes, proteins, lipids or carbohydrates, infectious agents such as viruses, bacteria or parasites, cell types present in the specimen, or toxins. The assay device can comprise an immunoassay device that utilizes antibodies specific for any chemical or biological reagent and any form of detection system known in the art. For example, methods of manufacturing antibodies and utilizing antibodies in immunoassay detection systems are described in Antibodies, A Laboratory Manual, edited by E. Harlow et al., Cold Spring Harbor Labs, Cold Spring Harbor, New York (1989), which incorporated by reference in its entirety. The assay The instant device can be used to collect samples of any solid or semi-solid material. These materials include biological samples, food samples, waste samples or soil samples. Biological samples refer to fecal samples, tissue samples, coagulated blood samples, mucous samples, saliva samples, stomach contents or the like.

The assay system with which the instant device is employed, may include antibodies that detect hemoglobin, antibodies that detect transferrin, or both. These antibodies can be used together with any immunodetection system known in the art. For example, both antibodies can be conjugated to a secondary reagent for detection. Secondary reagent means any substance that can be detected visually or with the aid of a device, thus effecting the detection of an antibody-analyte specific interaction. Methods suitable for the detection of analytes through antibody-analyte interactions include latex macro agglutination reactions, ELISA methods, radioimmunoassay (RIA) methods and the like. For example, immunoassay methods detecting hemoglobin and transferrin in fecal samples are described in H. Miyoshi et al., Immunological Determination of Fecal Hemoglobin and Transferorin Levels: A Comparison with Other Fecal Blood Tests, J. of Gastroenterology 87:67–73 (1992); R. Matsuse et al., Immunochemical Detection of Fecal Occult Blood by Latex-Agglutination Reaction for Hemoglobin and Transferrin, Saishin Igaku 44:2636–2641 (1989); and U.S. Pat. No. 4,920,045, issued Apr. 24, 1990, all herein incorporated by reference in their entirety.

The vial 1 can optionally contain a liquid sample-stabilizing reagent which dilutes and stabilizes the sample and may serve as an assay system reagent. The reagent can be saline, any buffered solution, or the like. The reagent can also contain a preservative, such as sodium azide at a concentration of about 0.1% weight per unit volume (w/v %) in an appropriate buffer used to maintain approximate physiological pH, such as Tris.

Another example of such a liquid sample-stabilizing reagent for an FOBT assay is a glycosidase type bacteriolytic enzyme. When a glycosidase type bacteriolytic enzyme is mixed with a fecal sample, the enzyme prevents the decomposition of hemoglobin by intestinal bacteria for a long period of time. In addition, said enzyme can detach hemoglobin from viscous components as well as bacterial cell wall components within a short time, thus increasing the amount of hemoglobin available for assay.

As the bacteriolytic enzyme, there may be used any one of glycosidase type, including enzyme F1 and enzyme 32 produced by *Streptomyces albus* G, enzyme $E_1$, enzyme $E_2$ and enzyme F2 produced by *Streptomyces griseus* and enzyme Mu I and enzyme MU II produced by *Streptomyces globisporus* 1829, lysozyme Ch produced by *Chalaropsis sp.*, bacterial lysozyme produced by *Bacillus subtilis* K-77, enzyme B produced by *Bacillus subtilis* YT-25, Fba-lysin produced by *Myxococcus Xanthus*, etc. These enzymes are commonly known, for instance, as described in Hunazu et al.: "Youkinkouso" (Bacteriolytic enzyme), page 93 (1983) and also readily available on the market. For instance, lysozyme obtained from the white of egg (manufactured by Sigma, St. Louis, Mich.) can be favorably employed for the purpose of this invention.

A general method for collecting, storing and processing and dispensing samples using the specimen handling device of the invention comprises the following steps. First, the sealable cap 4 with attached sample collection 2 means is separated from the sample storage means 1. Care should be taken not to spill the stabilizing solution, if present, from the sample storage means 1 or breaking the off the applicator tip 11. Next, a sample is collected with the specimen collection means by inserting the grooves 8 of the grooved sample collection means 2 into a sample. The collected sample should fill all of the channels in the grooves 8, yet not protrude beyond or above the grooves. Next, the grooved sample collection means 2 is inserted back into the vial 1, and the cap 4 is sealed back onto the vial 1. The specimen handling device is then optionally agitated to disperse sample into the liquid stabilizing reagent in the vial 1. The opening on the cap 4 is exposed by displacing or removing the removable applicator tip 11, as illustrated in FIGS. 5 and 6. Finally, positive pressure is applied to the vial 1 and drops of liquid sample are applied to an assay device, as illustrated in FIG. 7.

A specific testing procedure for the use of the invention in conjunction with a fecal occult blood test (FOBT) is summarized below. In particular, this procedure is that used with the LA Hemochaser® FOBT assay, available from Mizuho Medy Co., Ltd., S-4 Fusinoki-machi Tosu, Saga 841 Japan, and MIZUHO USA, Inc., 5555 Oberlin Drive, Suite 120, San Diego, Calif. 92121. The LA Hemochaser® assay system kit utilizes an immunoassay method which detects hemoglobin and transferrin in human fecal samples using a latex macro-agglutination detection. The system assay kit comprises a testing plate with a plurality of wells and a latex-immunoglobulin reagent. The reagent comprises two types of latex particles, or beads, one type conjugated to rabbit anti-human hemoglobin antibodies and the other type conjugated to rabbit anti-human transferrin antibodies, and a stabilizing solution, contained in the sample storage means of the device of FIG. 1.

EXAMPLE I

SPECIMEN COLLECTION

The following example illustrates one means by which the collection device of the invention, depicted in FIG. 1, can effectively collect, and store a specimen for future testing.

The specimen handling device (FIG. 1) of the invention was distributed to health care professionals or patients for the collection of fecal samples. Included with the specimen handling device are appropriate instructions for use.

A random sample of feces was placed on a clean, dry surface, making sure to exclude urine. The sealable cap 4 of the specimen handling device with attached grooved sample collection means 2, or sampling stick, was unscrewed from the vial 1. The cap and sampling stick was removed from the vial. Care was taken not to spill liquid sample-stabilizing solution from the vial and not to break off the removable applicator tip 11 of the applicator means from the cap's end.

The sampling stick was introduced into fecal sample several times at different sites. Visual inspection of the grooves of the sampling stick ensures that adequate sample deposited been thereon. In other words, sufficient sample was collected so that the sample filled the channels between the grooves 8, but did not extend above or beyond them. The sampling stick 2 was inserted into the vial 1 and tightly sealed. The specimen container was shaken again. Care was taken not to break off the removable applicator tip end 11. The sample was tested within one week of collection. If appropriate, specimen handling device was replaced into a storage box for transportation to a testing laboratory. If storage or shipment was necessary, the collection device and sample was kept at approximately 2° to 4° centigrade.

EXAMPLE II

DISPENSING OF SPECIMEN FROM SPECIMEN HANDLING DEVICE INTO THE ASSAY SYSTEM AND DETECTION OF HEMAGLOBIN AND TRANSFERRIN ANALYTES

The following example illustrates one means by which the specimen handling device of the invention can effectively apply a diluted and filtered sample to the assay system for fecal occult blood for analytical testing. As with Example 1, this procedure was performed with the LA Hemochaser® kit.

Immediately before the testing reaction was done, the specimen handling device was agitated. The applicator tip 11 was carefully broken off or displaced from the cap 4. Only slight lateral, or shear, force was necessary. The applicator tip could be displaced to varying degrees. (The extent of displacement determined the size of the opening at the hollow core 12 thus allowing the operator to control the size of the drop that was formed upon dispensing the liquid sample.) Next, the specimen handling device was inverted and the vial was gently squeezed. The sample was forced through the filter means 3 by this pressure. The first two or three drops that were expelled from the applicator tip were discarded and one drop of filtered, liquid specimen was placed on the testing plate well.

Figure 8:
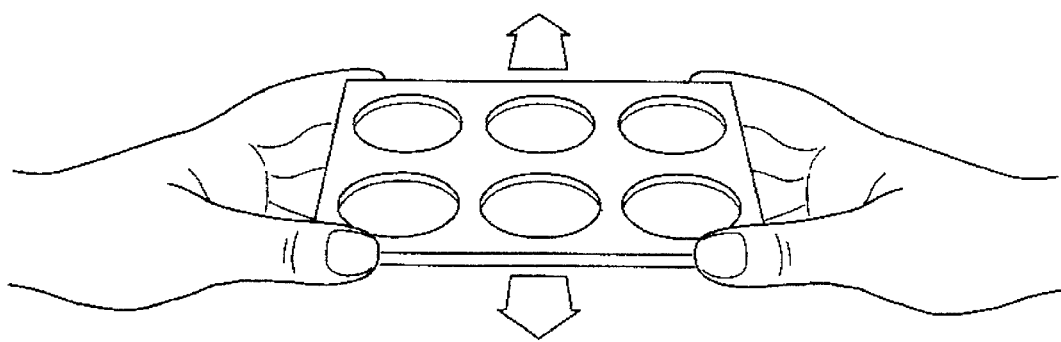
FIG. 8 is a view of a testing plate well being agitated after application of sample into the testing plate's wells.

Next, the latex reagent was re-suspended by gentle agitation or swirling. One drop of the latex-bead/antibody reagent was added to the testing plate well. The testing plate well was gently rotated until the mixture of specimen and reagent completely covered the well. A reaction mixture spreading stick was used for mixing the reaction mixture and spreading it over the testing plate well. The timer was started, the slide containing the testing plate wells was rocked gently (FIG. 8) for 3 minutes and the wells promptly observed for macroagglutination. If hemoglobin and/or transferrin were present in the sample, the analyte/antibody interaction would cause the antibody-conjugated latex beads to macroagglutinate. This reaction was visible to the naked eye. The sample handling device was then discarded.

EXAMPLE III

DETECTING ANALYTE WITH AN ASSAY SYSTEM

The following example illustrates a use of the specimen collection with an assay system to effectively detect an analyte in the filtered and dispensed liquid sample. The results in the following Table are those set forth in Ryoichi Matsuse et al., *Osaka, Saishin-Igaku*, "Immunochemical Detection of Fecal Occult Blood by Latex Agglutination Reaction for Hemoglobin and Transferrin", 44(12):2636 (1989). The table depicts the results obtained with the LA Hemochaser® but, using the instant device (FIG. 1).

TABLE 1

| | | POSITIVE RATE FOR VARIOUS MAKERS TESTS FOR 3 DAYS TESTING | | | | |
|---|---|---|---|---|---|---|
| METHOD DISEASE | NUMBER OF SAMPLES | RPHA | Hb LATEX* | EIA | Guaiac | LA HEMOCHASER |
| Cancer | 13 | 13 (100.0%) | 10 (76.9%) | 12 (92.3%) | 10 (76.9%) | 13 (100.0%) |
| Polyp | 31 | 10 (32.3%) | 7 (22.6%) | 17 (54.8%) | 16 (51.6%) | 21 (67.7%) |
| Control | 46 | 8 (17.4%) | 1 (2.2%) | 8 (17.4%) | 13 (28.3%) | 2 (4.3%) |

*Another manufacturer's latex agglutination immunoassay (for detection of hemoglobin only).

Many other objects, features, and advantages of the present invention will be apparent to those of skill in the art. Although the invention has been described with reference to the figures and Examples provided above, it should be understood that various modifications can be made by those skilled in the art without departing from the invention. Accordingly, the invention is set out in the following claims.

We claim:

1. A specimen handling device comprising:

a sample storage means, a sample collection means, a filter means, a sealable cap and an applicator means;

said sample storage means having a length longer than said sample collection means having one opening containing a sealing means upon which attaches said sealable cap;

said sample collection means comprising an elongated shaft with a grooved sample collection means at one end and a cap end attached to said sealable cap;

said grooved sample collection means containing a plurality of grooves extending parallel to and along the length of said elongated shaft;

said sealable cap comprising a hollow interior through which sample flows from said sample storage means to said applicator means;

said filter means contained entirely within said sealable cap through which liquid passes to flow from said sample storage means to said applicator means;

said applicator means comprising a removable applicator tip with a hollow core where displacement of said applicator tip creates an opening on the top of said sealable cap.

2. A specimen handling device according to claim 1, wherein the filter means is selected from the group consisting of a sponge material or a screen material.

3. A specimen handling device according to claim 2, wherein the filter means is a sponge material made of polyurethane.

4. A specimen handling device of claim 1, wherein the sample storage means is polyethylene.

5. A specimen handling device of claim 1, wherein the sample collection means is polystyrene.

6. A specimen handling device of claim 1, wherein the sealable cap is polypropylene.

7. A specimen handling device of claim 1, wherein a liquid sample-stabilizing reagent is contained in the sample storage means.

8. A specimen handling device of claim 7, wherein the liquid sample-stabilizing reagent stabilizes hemoglobin.

9. A specimen handling device of claim 8, wherein the liquid sample-stabilizing reagent that stabilizes hemoglobin contains a glycosidase capable of lysing bacterial cells.

10. A specimen handling device of claim 9, wherein the glycosidase is lysozyme.

11. A specimen handling device of claim 8, wherein the hemoglobin liquid sample-stabilizing reagent consists of sodium azide and Tris buffer.

\* \* \* \* \*